(12) United States Patent
Jiang et al.

(10) Patent No.: US 12,029,612 B2
(45) Date of Patent: Jul. 9, 2024

(54) ULTRASONIC DEVICE FOR COUPLING AN ULTRASONIC COUPLING GEL AND ULTRASONIC HEAD

(71) Applicant: JKH Health Co., Ltd, Shenzhen (CN)

(72) Inventors: Pu Jiang, Shenzhen (CN); Baohua Jiang, Shenzhen (CN); Quanqin Dai, Irvine, CA (US)

( * ) Notice: Subject to any disclaimer, the term of this patent is extended or adjusted under 35 U.S.C. 154(b) by 0 days.

(21) Appl. No.: 18/300,292

(22) Filed: Apr. 13, 2023

(65) Prior Publication Data
US 2023/0380803 A1 Nov. 30, 2023

(51) Int. Cl.
*A61B 8/00* (2006.01)

(52) U.S. Cl.
CPC .......... *A61B 8/4281* (2013.01); *A61B 8/4444* (2013.01)

(58) Field of Classification Search
None
See application file for complete search history.

(56) References Cited

U.S. PATENT DOCUMENTS

| | | | | |
|---|---|---|---|---|
| 2005/0240102 A1* | 10/2005 | Rachlin | | A61B 8/10 600/459 |
| 2013/0144193 A1* | 6/2013 | Lewis, Jr. | | A61B 8/4281 601/2 |
| 2014/0180116 A1* | 6/2014 | Lindekugel | | A61B 8/4455 600/459 |
| 2014/0236016 A1* | 8/2014 | Morgan | | A61B 8/4483 600/459 |
| 2014/0276077 A1* | 9/2014 | Morgan | | A61B 8/4281 600/459 |
| 2014/0336512 A1* | 11/2014 | Mehi | | A61B 8/4483 600/443 |
| 2019/0247679 A1* | 8/2019 | Vincenot | | A61B 8/4444 |

FOREIGN PATENT DOCUMENTS

| | | | |
|---|---|---|---|
| CN | 107616813 A | * 1/2018 | |
| WO | WO-2014156258 A1 | * 10/2014 | ........... A61B 8/4411 |

OTHER PUBLICATIONS

WO2014156258A1 (Hitachi Aloka Medical Ltd). Translated by Espacenet. Mar. 27, 2013. [retrieved May 16, 2023] (Year: 2013).*
CN107616813A (Shenzhen Qianzhikang Medical Product Co Ltd) Translated by Espacenet. Nov. 10, 2017. [retrieved May 17, 2023] (Year: 2017).*

* cited by examiner

Primary Examiner — Colin T. Sakamoto
Assistant Examiner — Andrew W Begeman
(74) Attorney, Agent, or Firm — Arch & Lake LLP

(57) ABSTRACT

The present invention discloses an ultrasonic device including an ultrasonic head protruding from a body, a fixing piece and an ultrasonic coupling gel. The fixing piece includes a cover plate and a peripheral wall circumferentially connected with the cover plate. The peripheral wall is sleeved on the ultrasonic head to realize the connection between the fixing piece and the ultrasonic head, and at the same time, an accommodation space is formed between the ultrasonic head and the cover plate. The ultrasonic coupling gel includes a connecting part that is accommodated in the accommodation space and respectively attached to the ultrasonic head and the cover plate. The close connection between the ultrasonic coupling gel and the ultrasonic head is realized by arranging the connecting part between the ultrasonic head and the cover plate, so that the force on the connecting part is more uniform.

20 Claims, 11 Drawing Sheets

ULTRASONIC DEVICE FOR COUPLING AN ULTRASONIC COUPLING GEL AND ULTRASONIC HEAD

CROSS-REFERENCES TO RELATED APPLICATIONS

This non-provisional application claims priority under 35 U.S.C. § 119(a) on China Utility Model Patent No(s). CN 217696625U filed on May 25, 2022, the entire contents of which are hereby incorporated by reference.

FIELD OF THE INVENTION

The present invention relates to the technical field of medical instruments, in particular to an ultrasonic device.

BACKGROUND OF THE INVENTION

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon.

Existing ultrasound devices generally include an ultrasound head and an ultrasound coupling gel, and the ultrasound generated by the ultrasound head can act on the treatment site through the ultrasound coupling gel in contact with the skin. Ultrasonic coupling gel is generally in a liquid state and is inconvenient to clean. It is also possible to use solid-state ultrasonic coupling gel, which is a large piece of solid-state ultrasonic coupling gel that attaches on the human body, which is inconvenient to fix and high in cost.

SUMMARY

In order to solve the problem above, it is necessary to provide an ultrasonic device aimed at solving the technical problem of inconvenient use or high cost of the ultrasonic coupling gel in the existing ultrasonic device.

The present invention provides an ultrasound device, comprising:
a body;
an ultrasonic head, which protrudes from the body and capable of generating ultrasound;
a fixing piece, which includes a cover plate and a peripheral wall circumferentially connected with the cover plate; the peripheral wall is sleeved on the ultrasonic head to form an accommodation space between the ultrasonic head and the cover plate; a through hole is provided on the cover plate, and the through hole communicates with the accommodation space; and
an ultrasonic coupling gel, which is used for ultrasound to pass through, the ultrasonic coupling gel includes a connecting part and a protruding part; the connecting part is accommodated in the accommodation space and attached to the ultrasonic head and the cover plate respectively; the protruding part is arranged on the connecting part and is exposed outside the fixing piece through the through hole.

In another aspect, the ultrasonic coupling gel is in a solid gel state, including but not limited to coupling gels, aqueous polymer gels, acrylic resin gels, or solid gels of other materials.

In another aspect, the bit or tool holder attachment further comprising a casing, which covers the main body, and the casing is provided with an accommodating hole corresponding to the position of the hole, so that the bit or tool holder can pass through and be placed outside the casing.

In another aspect, the ultrasonic head is provided with an annular notch to form a stepped portion on the ultrasonic head, and a side of the peripheral wall that is away from the cover plate is complementary to the annular notch.

In another aspect, the peripheral wall is magnetically connected to the ultrasonic head.

In another aspect, the peripheral wall elastically abuts against the ultrasonic head, a vacant portion is provided on a side of the peripheral wall that is away from the cover plate, and the vacant portion penetrates through the peripheral wall.

In another aspect, the ultrasonic head is provided with a first clamping part, and the peripheral wall is provided with a second clamping part, and the second clamping part is clamped with the first clamping part, so that the peripheral wall is sleeved on the ultrasonic head.

In another aspect, the side of the peripheral wall that is away from the cover plate is provided with a plurality of through grooves, and the through grooves penetrate through the peripheral wall to form elastic arm between adjacent through grooves, and the second clamping part is arranged on the elastic arm.

In another aspect, the first clamping part is an annular structure.

In another aspect, the protruding part is attached to inner wall of the through hole on the cover plate.

In another aspect, the ultrasonic head includes a first surface, and the connecting part is bonded to the first surface, the first surface is a plane surface or a curved surface.

Implementing the embodiments of the present invention will have following beneficial effects:

The above-mentioned ultrasonic device, in addition to having excellent ultrasonic performance, can also realize the rapid assembly of the ultrasonic coupling gel, and avoid the bending of the ultrasonic coupling gel during the assembly process, thereby avoiding the ultrasonic coupling gel from breaking during the subsequent use of the ultrasonic device. Specifically, the ultrasonic device includes an ultrasonic head protruding from the body, a fixing piece, and an ultrasonic coupling gel, while the body can be connected with other devices by using an output line or wirelessly connected with other devices. Wherein, the fixing piece includes a cover plate and a peripheral wall circumferentially connected with the cover plate, and the peripheral wall is sleeved on the ultrasonic head, so as to realize the connection between the fixing piece and the ultrasonic head, and at the same time form an accommodation space between the ultrasonic head and the cover plate. The ultrasonic coupling gel includes a connecting part that is accommodated in the accommodation space and respectively attached to the ultrasonic head and the cover plate, so that when the ultrasonic coupling gel is connected to the ultrasonic head, bending of the ultrasonic coupling gel can be avoided. By arranging the connecting part between the ultrasonic head and the cover plate to form a close connection between the ultrasonic coupling gel and the ultrasonic head, the force on the connecting part will be more uniform, avoiding or reducing stress concentration, and thus reducing the risk of fracture of the ultrasonic coupling gel. Further, the cover plate is provided with a through hole, and the connecting part is provided with a protruding part that can be exposed outside the fixing piece through the through hole, so that the protruding part can contact the skin and reduce the friction between the ultrasonic head and the skin so that the ultrasonic head can slide flexibly and is easy to clean, and the ultrasound generated by the ultrasonic head can act on the treatment site through the ultrasonic coupling gel.

Other systems, devices, methods, features, and advantages will be or become apparent to one with skill in the art upon examination of the following drawings and detailed description. It is intended that all such additional systems, methods, features, and advantages be included within this description, be within the scope of the present disclosure, and be protected by the accompanying claims and drawings.

BRIEF DESCRIPTION OF THE DRAWINGS

The invention will now be described, by way of example, with reference to the accompanying drawings, in which.

Like reference numerals refer to like parts throughout the various views of the drawings.

DETAILED DESCRIPTION OF THE INVENTION

Figure 1:
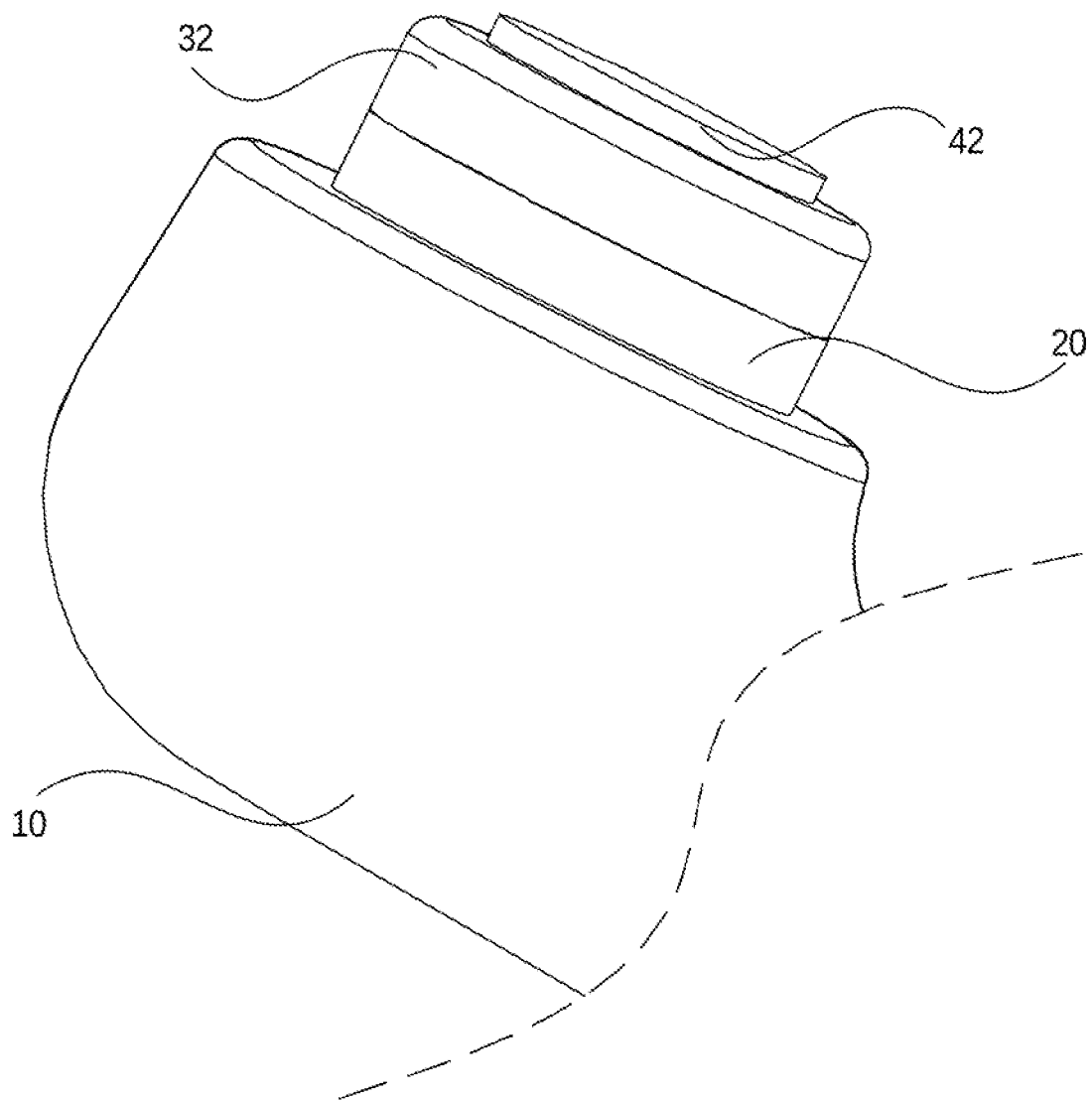
FIG. 1 is a partial schematic diagram of an ultrasonic device in a first embodiment.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper," "lower," "left," "rear," "right," "front," "vertical," "horizontal," and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Specific dimensions and other physical characteristics relating to the embodiments disclosed herein are therefore not to be considered as limiting, unless the claims expressly state otherwise.

In addition, terms such as "first" and "second" are used only for distinguishing descriptions and should not be understood as indicating or implying relative importance. It should be noted that, in the case of no conflict, the features in the embodiments of the present invention can be combined with each other.

Existing ultrasound devices generally include an ultrasound head and an ultrasound coupling gel, and the ultrasound generated by the ultrasound head can act on the treatment site through the ultrasound coupling gel in contact with the skin. Ultrasonic coupling gel is generally in a liquid state and is inconvenient to clean. It is also possible to use solid-state ultrasonic coupling gel, which is a large piece of solid-state ultrasonic coupling gel that attaches on the human body, which is inconvenient to fix and high in cost.

In order to solve the above-mentioned technical problems, the present invention provides an ultrasonic device, which can generate ultrasound and can be attached to the skin and apply the ultrasound to the treatment site.

Please refer to FIG. 1 and FIG. 2 together, and the ultrasonic device provided by the present invention will be described. The ultrasonic device includes a body 10, an ultrasonic head 20, a fixing piece 30, and an ultrasonic coupling gel 40. Wherein, the body 10 can be a holding structure, so as to facilitate holding the ultrasonic device and placing the ultrasonic device on different parts of the human body. In this embodiment, the body 10 is in the shape of a handle. A cavity is provided inside the body 10 for installation of electrical components such as circuit boards and power supplies. It can be understood that in other embodiments, the body 10 can also be another carrier structure for carrying the ultrasonic head 20, the fixing piece 30, and the ultrasonic coupling gel 40, such as the structure of connecting the ultrasonic head 20 with an output line or the structure of connecting the ultrasonic head 20 through wireless.

Further, the ultrasonic head 20 protrudes from the body 10. The ultrasound head 20 is capable of generating ultrasound. The fixing piece 30 includes a cover plate 31 and a peripheral wall 32 circumferentially connected with the cover plate 31. The peripheral wall 32 is sleeved on the ultrasonic head 20 to form an accommodation space between the ultrasonic head 20 and the cover plate 31. A through hole 100 is defined on the cover plate 31. The through hole 100 communicates with the accommodation space. The ultrasonic coupling gel 40 is used for ultrasonic transmission. The ultrasonic coupling gel 40 includes a connecting part 41 and a protruding part 42, the connecting part 41 is accommodated in the accommodation space and attached to the ultrasonic head 20 and the cover plate 31 respectively. The ultrasonic head 20 is attached to the connecting part 41 to improve the efficiency of ultrasonic transmission. Further, the protruding part 42 is disposed on the connecting part 41 and can be exposed outside the fixing piece 30 through the through hole 100. The ultrasonic head 20 is protruded from the body so that the protruding part 42 can be more easily attached to the skin to ensure the conduction of the ultrasound. In this embodiment, the ultrasonic coupling gel 40 is made of solid coupling gel. The ultrasonic coupling gel 40 has a certain degree of elasticity, so as to improve the comfort of contact with the skin and avoid scratching the skin. At the same time, the ultrasonic coupling gel 40 has the contact between the ultrasonic head 20 and the skin to reduce acoustic resistance, reduce the reflection loss of ultrasonic energy on the skin, and play a lubricating role. It can be understood that in other embodiments, the ultrasonic coupling gel 40 can be replaced by other solid gels, including but not limited to coupling gels, aqueous polymer gels, acrylic resin gels, or solid gels made of other materials.

To sum up, the implementation of the embodiment of the present invention will have the following beneficial effects: the above-mentioned ultrasonic device, in addition to having excellent ultrasonic performance, can also realize the rapid assembly of the ultrasonic coupling gel 40, and avoid the bending of the ultrasonic coupling gel 40 during the assembly process, thereby avoiding the ultrasonic coupling gel 40 from breaking during the subsequent use of the ultrasonic device. Specifically, the ultrasonic device includes an ultrasonic head 20 protruding from the body 10, a fixing piece 30, and an ultrasonic coupling gel 40. Wherein, the fixing piece includes a cover plate 31 and a peripheral wall 32 circumferentially connected with the cover plate 31, and the peripheral wall 32 is sleeved on the ultrasonic head 20, so as to realize the connection between the fixing piece 30 and the ultrasonic head 20, and at the same time form an accommodation space between the ultrasonic head 20 and the cover plate 31. The ultrasonic coupling gel 40 includes a connecting part 41 that is accommodated in the accommodation space and respectively attached to the ultrasonic head 20 and the cover plate 31, so that when the ultrasonic coupling gel 40 is connected to the ultrasonic head 20, bending of the ultrasonic coupling gel 40 can be avoided. By arranging the connecting part 41 between the ultrasonic head and the cover plate 31 to form a close connection between the ultrasonic coupling gel 40 and the ultrasonic head 20, the force on the connecting part 41 will be more uniform, avoiding or reducing stress concentration, and thus reducing the risk of fracture of the ultrasonic coupling gel 40. Further, the cover plate 31 is provided with a through hole 100, and the connecting part 41 is provided with a protruding part 42 that can be exposed outside the fixing piece 30 through the through hole 100, so that the protruding part 42 can contact the skin and reduce the friction between the ultrasonic head 20 and the skin so that the ultrasonic head 20 can slide flexibly and is easy to clean, and the ultrasound generated by the ultrasonic head 20 can act on the treatment site through the ultrasonic coupling gel 40.

In one embodiment, please refer to FIG. 1 to FIG. 5, the ultrasonic head 20 is provided with an annular notch 200 to form a stepped portion on the ultrasonic head 20, and the side of the peripheral wall 32 away from the cover plate 31 is complementary to the annular notch 200. In this way, by making the annular notch 200 complementary, it can ensure that the outer wall of the fixing piece 30 is flush with the outer wall of the ultrasonic head 20, thereby improving the overall appearance of the ultrasonic device. The stepped portion formed at the same time acts as a stopper to limit the movement of the fixing piece 30 to the side of the ultrasonic head 20, thereby reducing the size of the accommodation space and causing the connecting part 41 to be deformed or even crushed.

Figure 2:
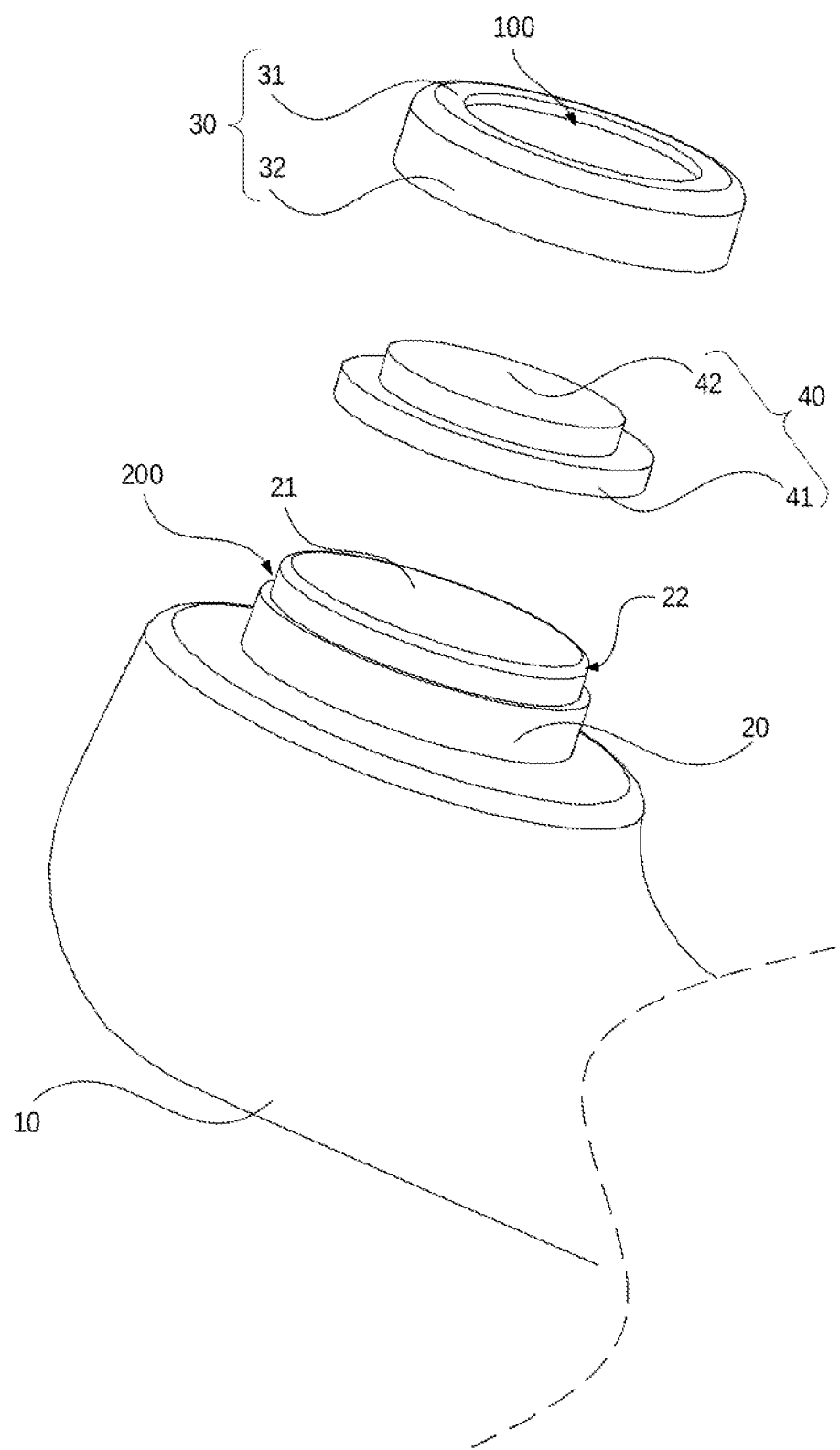
FIG. 2 is an exploded view of FIG. 1.

In one embodiment, please refer to FIG. 1 and FIG. 2 together, the peripheral wall 32 is magnetically connected to the ultrasonic head 20. This can facilitate the fast installation of the fixing piece 30 and the ultrasonic head 20, and realize the relative movement of the fixing piece and the ultrasonic head 20 under the action of magnetic force, so as to automatically move to a preset position. In this embodiment, the peripheral wall 32 and the ultrasonic head 20 can be respectively provided with a plurality of magnetic attractors, and the magnetic attractors are evenly distributed along the circumferential direction of the peripheral wall 32 and the ultrasonic head 20, so as to ensure the force between the fixing piece 30 and the ultrasonic head 20 is uniform. In addition, additional magnetic attractor(s) can be added on the end of the peripheral wall 32 away from the cover plate 31 and on the stepped portion to further improve the connection stability between the fixing piece 30 and the ultrasonic head 20, and at the same time make the end of the peripheral wall 32 away from the cover plate 31 is more closely fitted to the stepped portion, thereby improving the overall appearance. Further, there is a round transition between the peripheral wall 32 and the cover plate 31 to reduce the risk of the ultrasonic device scratching the skin.

Figure 3:
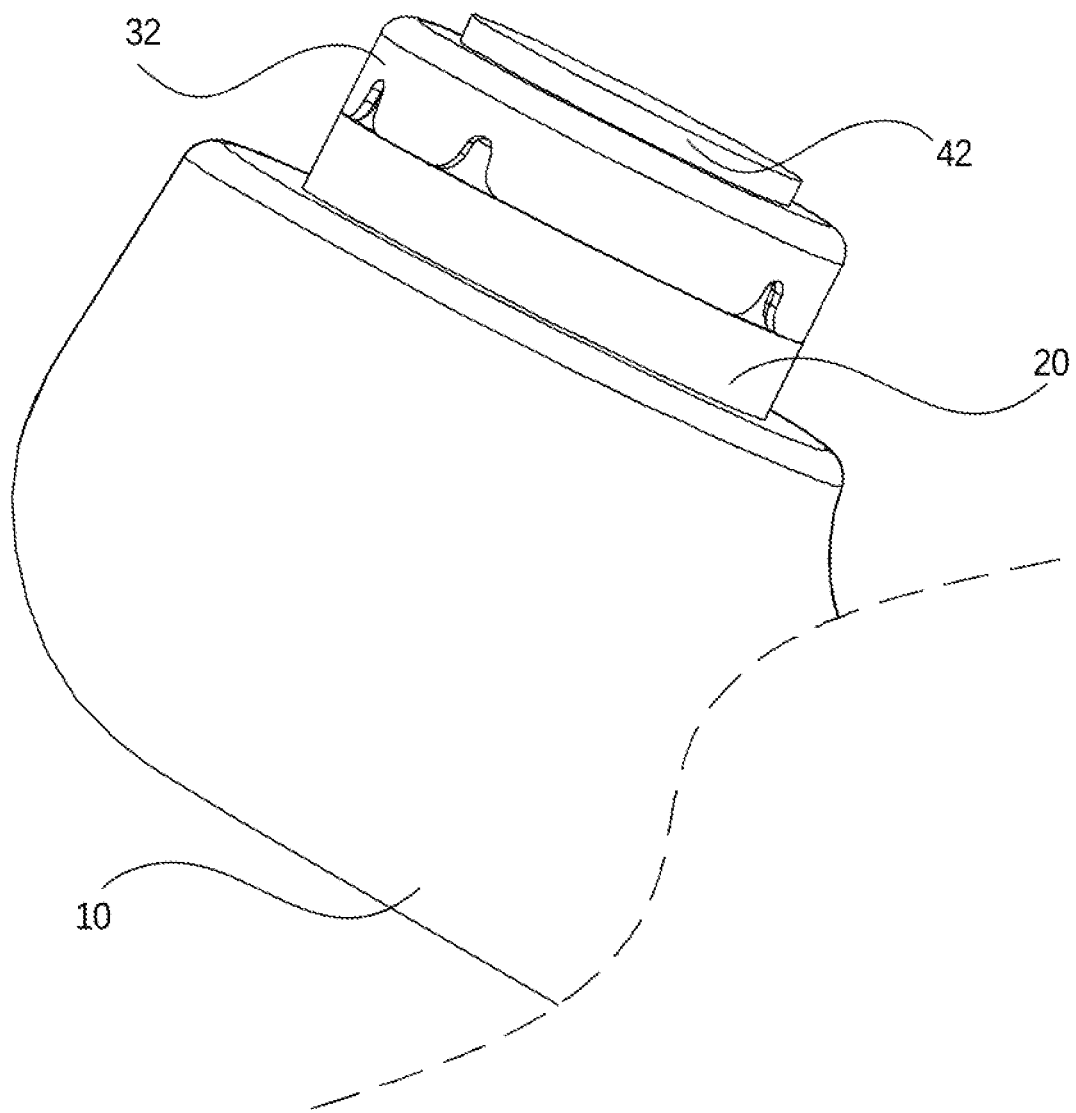
FIG. 3 is a partial schematic diagram of an ultrasonic device in a second embodiment.
Figure 4:
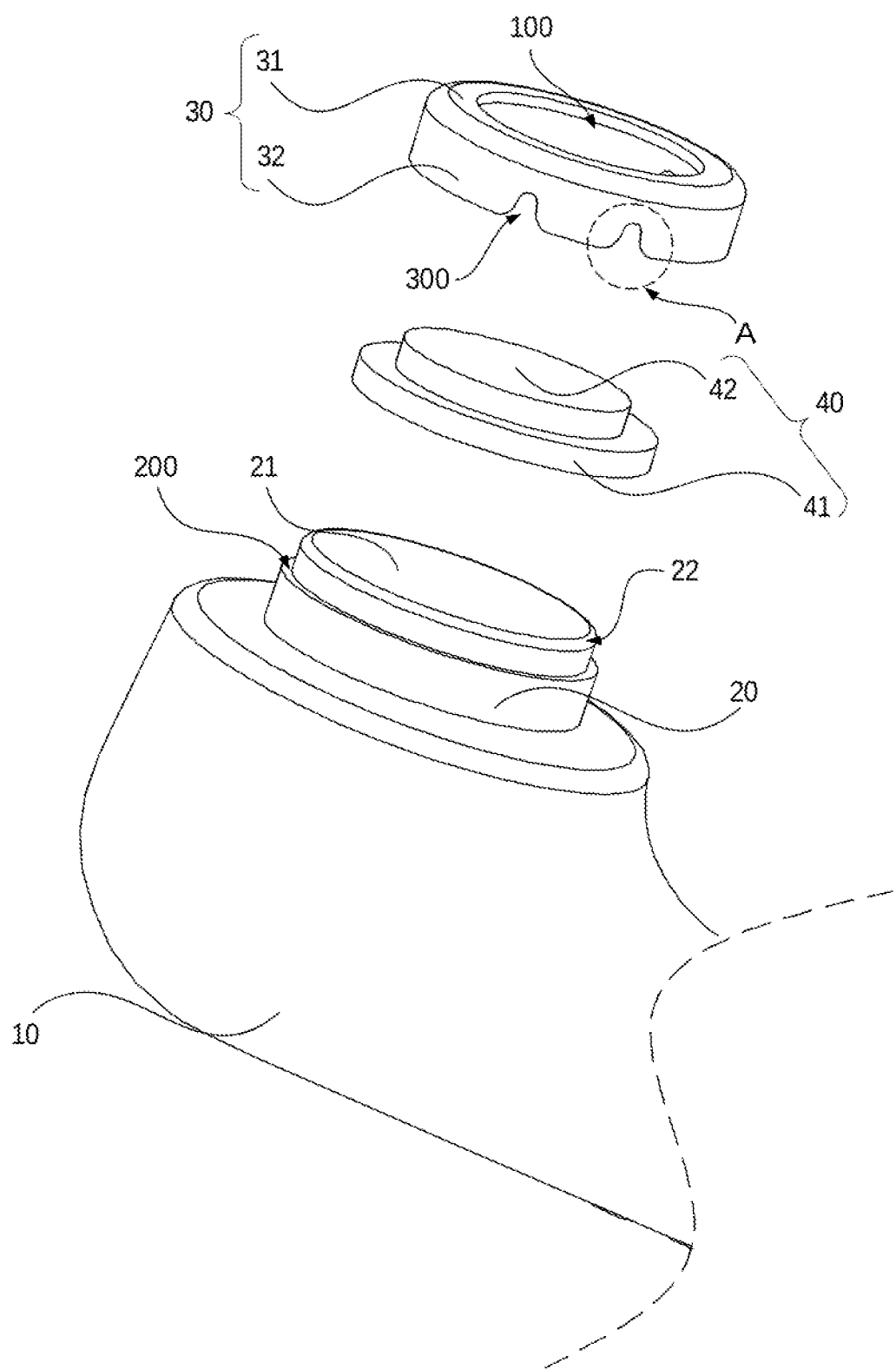
FIG. 4 is an exploded view of FIG. 3.
Figure 5:
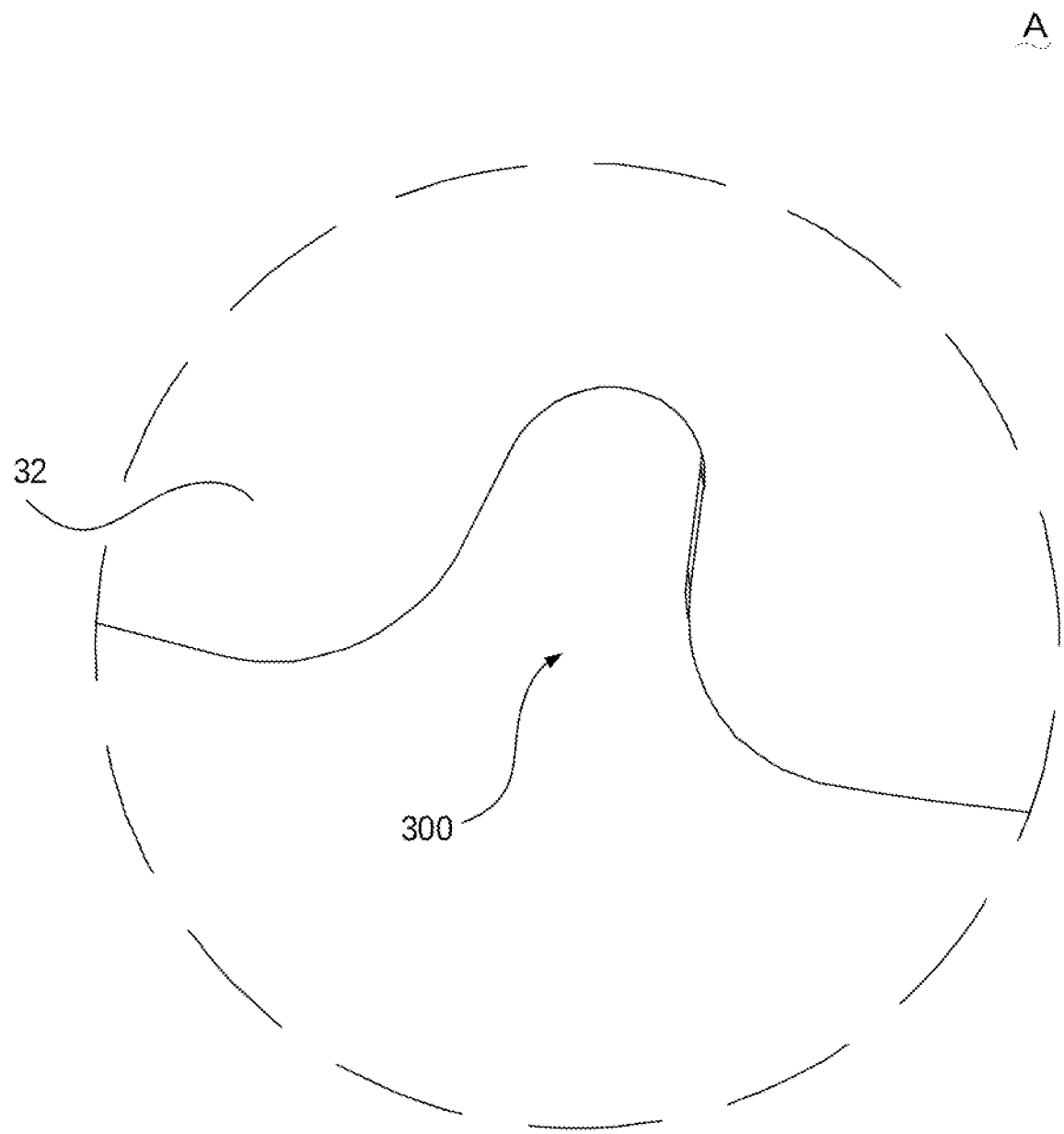
FIG. 5 is a schematic diagram of the enlarged structure of part A in FIG. 4.
Figure 6:
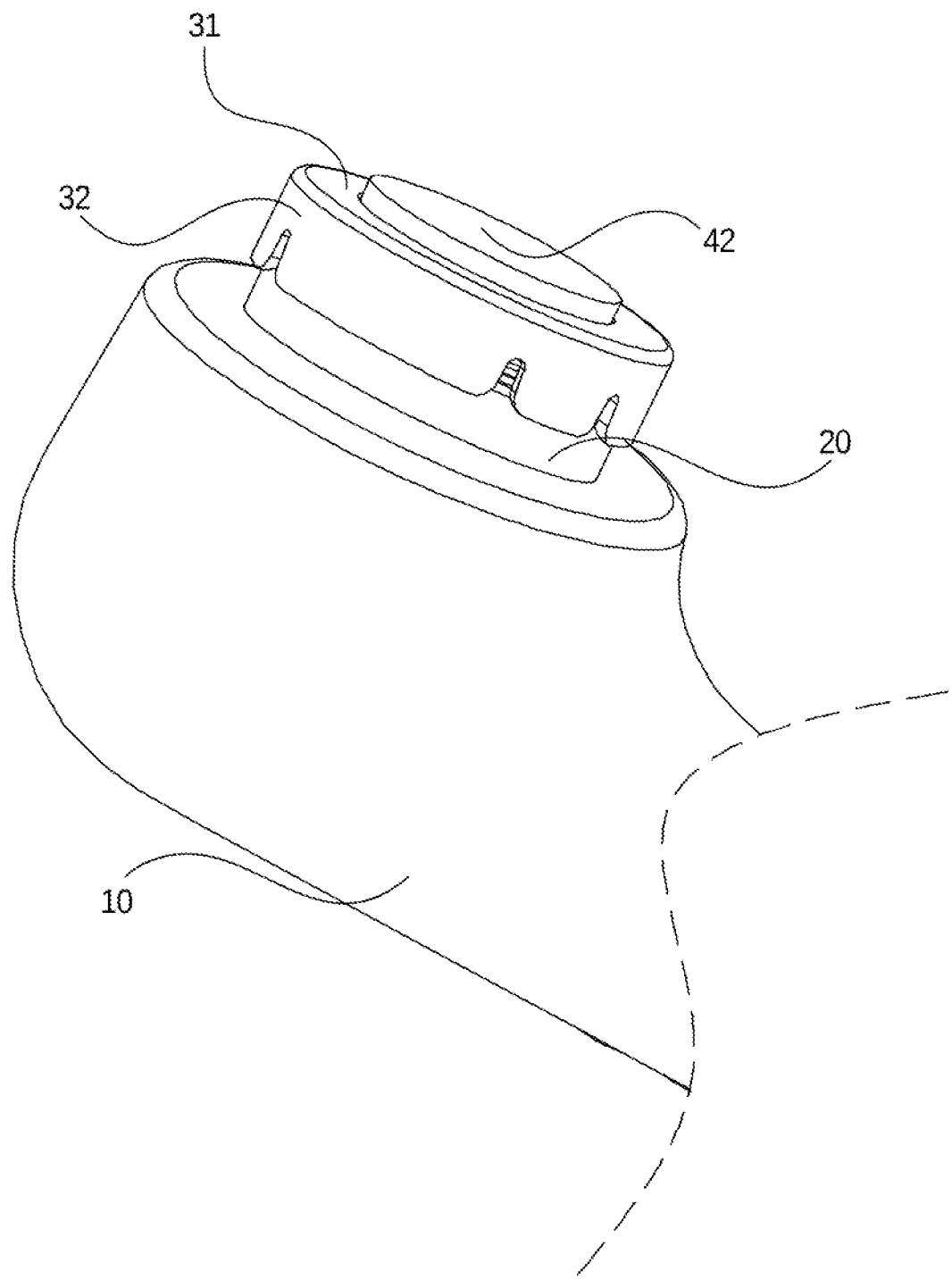
FIG. 6 is a partial schematic diagram of an ultrasonic device in a third embodiment.

In another embodiment, please refer to FIG. 3 to FIG. 5 together, the peripheral wall 32 elastically abuts the ultrasonic head 20. In this way, the socket between the fixing piece 30 and the ultrasonic head 20 is realized through the elastic abutment of the peripheral wall 32. Further, a vacant portion 300 is provided on a side of the peripheral wall 32 away from the cover plate 31, and the vacant portion 300 penetrates through the peripheral wall 32. In this way, the setting of the vacant portion 300 can reduce the rigidity of the peripheral wall 32 and increase the elastic force of the peripheral wall 32 to ensure the stability of the connection between the fixing piece 30 and the ultrasonic head 20. As shown in FIG. 5, further, the end of the vacant portion 300 close to the cover plate 31 is arc-shaped, so as to avoid fracture at the end of the vacant portion 300 close to the cover plate 31 when the peripheral wall 32 is deformed by force. There is a circular arc transition between the two sides of the vacant portion 300 away from the end of the cover plate 31 and the peripheral wall 32. When replacing the ultrasonic coupling gel 40, the above setting can avoid scratching fingers when separating the fixing piece 30 from the ultrasonic head 20. Further, the above setting makes the vacant portion 300 have a small end close to the end of the cover plate 31 and a large end far away from the end of the cover plate 31, so as to facilitate the elastic deformation of the peripheral wall 32. Further, there is a round transition between the peripheral wall 32 and the cover plate 31 to reduce the risk of the ultrasonic device scratching the skin.

In yet another embodiment, please refer to FIG. 6 to FIG. 10 together. The ultrasonic head 20 is provided with a first clamping part 400, and the peripheral wall 32 is provided with a second clamping part 321. The second clamping part 321 can be connected to the first clamping part 400, so that the peripheral wall 32 is sleeved on the ultrasonic head 20. In this way, the arrangement of the second clamping part 321 and the first clamping part 400 can increase the connection area between the fixing piece 30 and the ultrasonic head 20, thereby increasing the connection stability between the fixing piece 30 and the ultrasonic head 20. At the same time, the setting of the second clamping part 321 and the first clamping part 400 can restrict the fixing piece 30 from continuing to move toward the side of the ultrasonic head 20, and act as a stopper to limit the fixing piece 30 from continuing to move toward the side of the ultrasonic head 20, and then reduce the size of the accommodation space, causing the connecting part 41 to be squeezed, deformed, or even crushed. In this embodiment, the first clamping part 400 is a groove structure. The second clamping part 321 is a protruding structure. It can be understood that in other embodiments, the first clamping part 400 is a protruding structure, and the second clamping part 321 is a groove structure.

Figure 7:
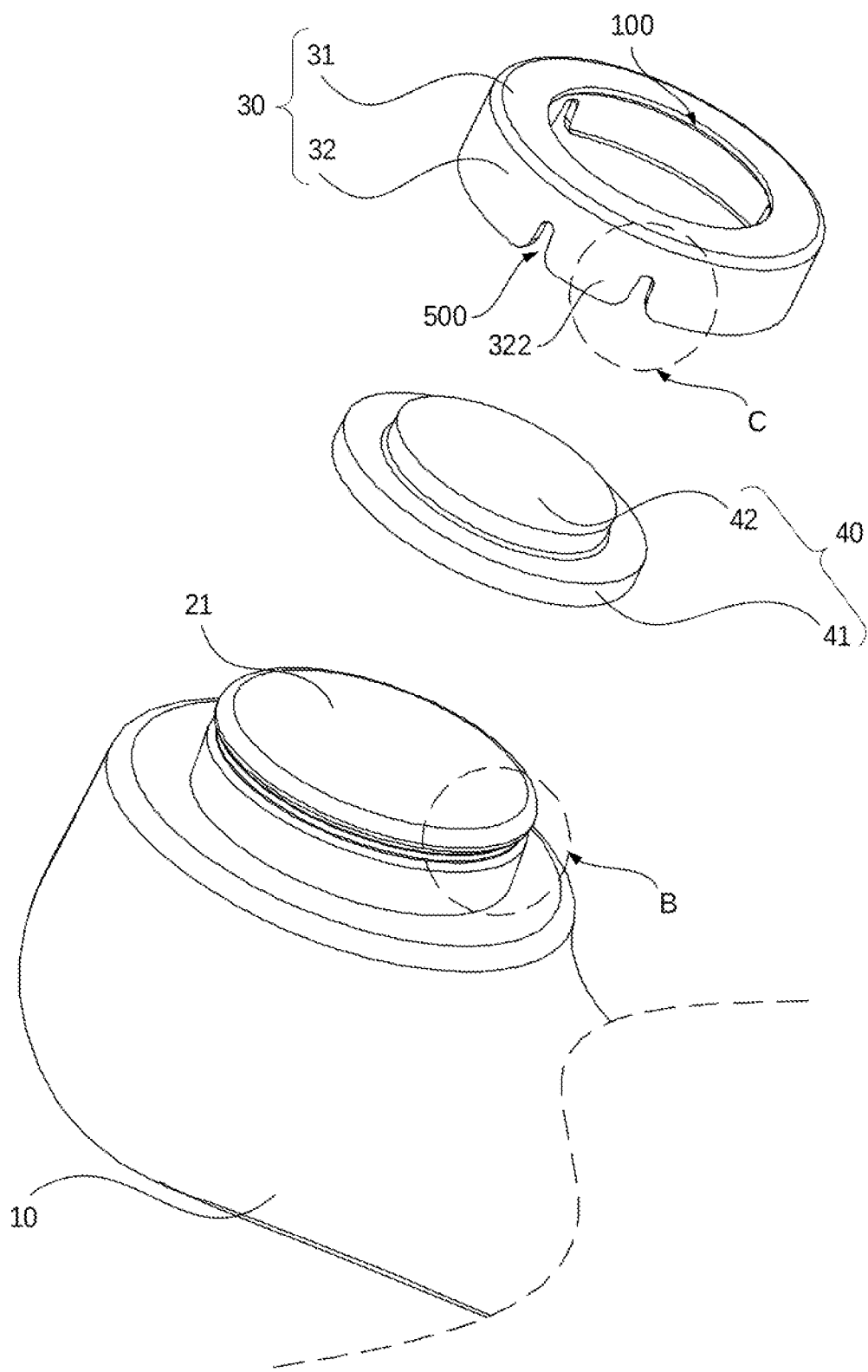
FIG. 7 is an exploded view of FIG. 6.
Figure 8:
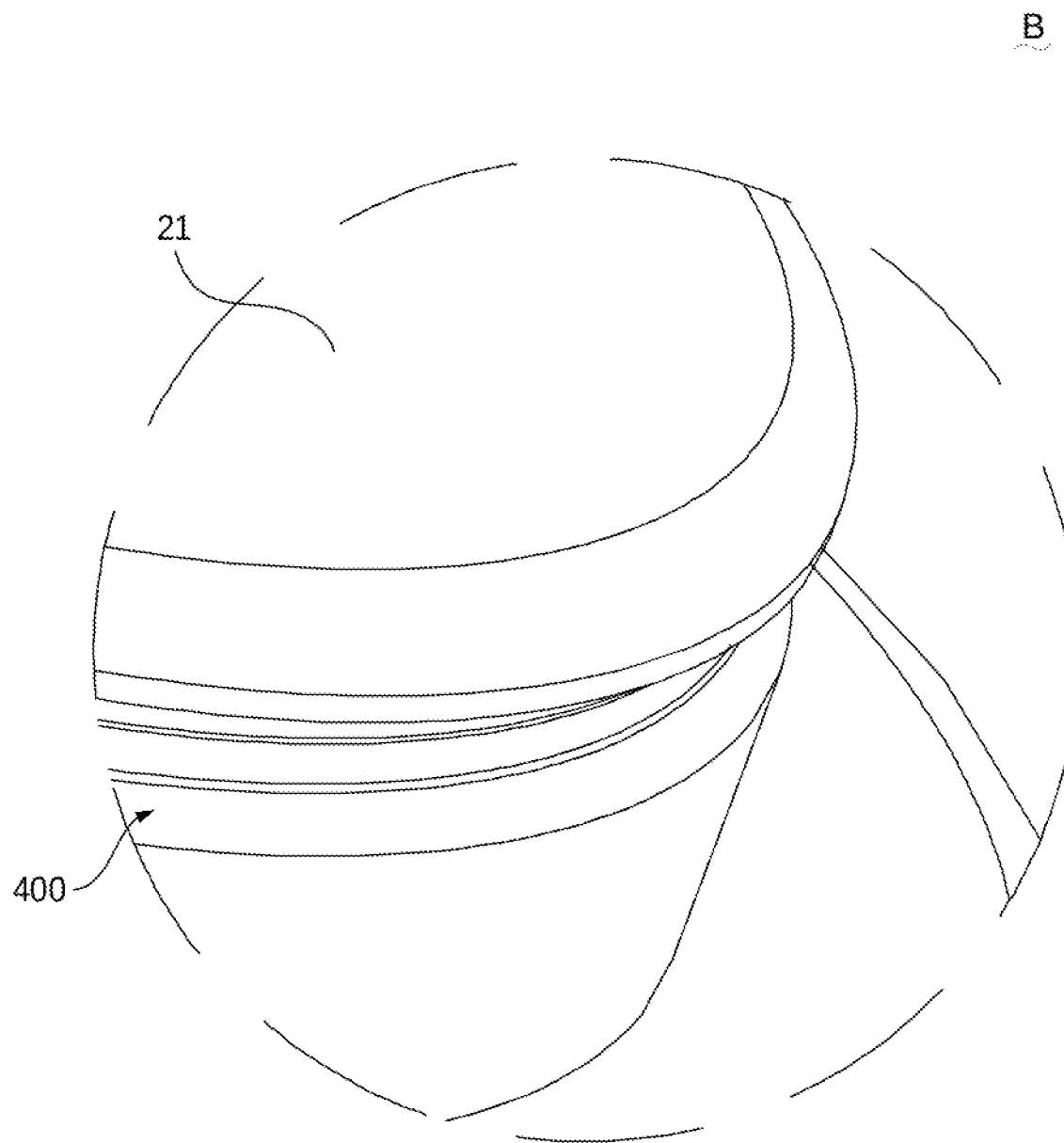
FIG. 8 is a schematic diagram of the enlarged structure of part B in FIG. 7.
Figure 9:
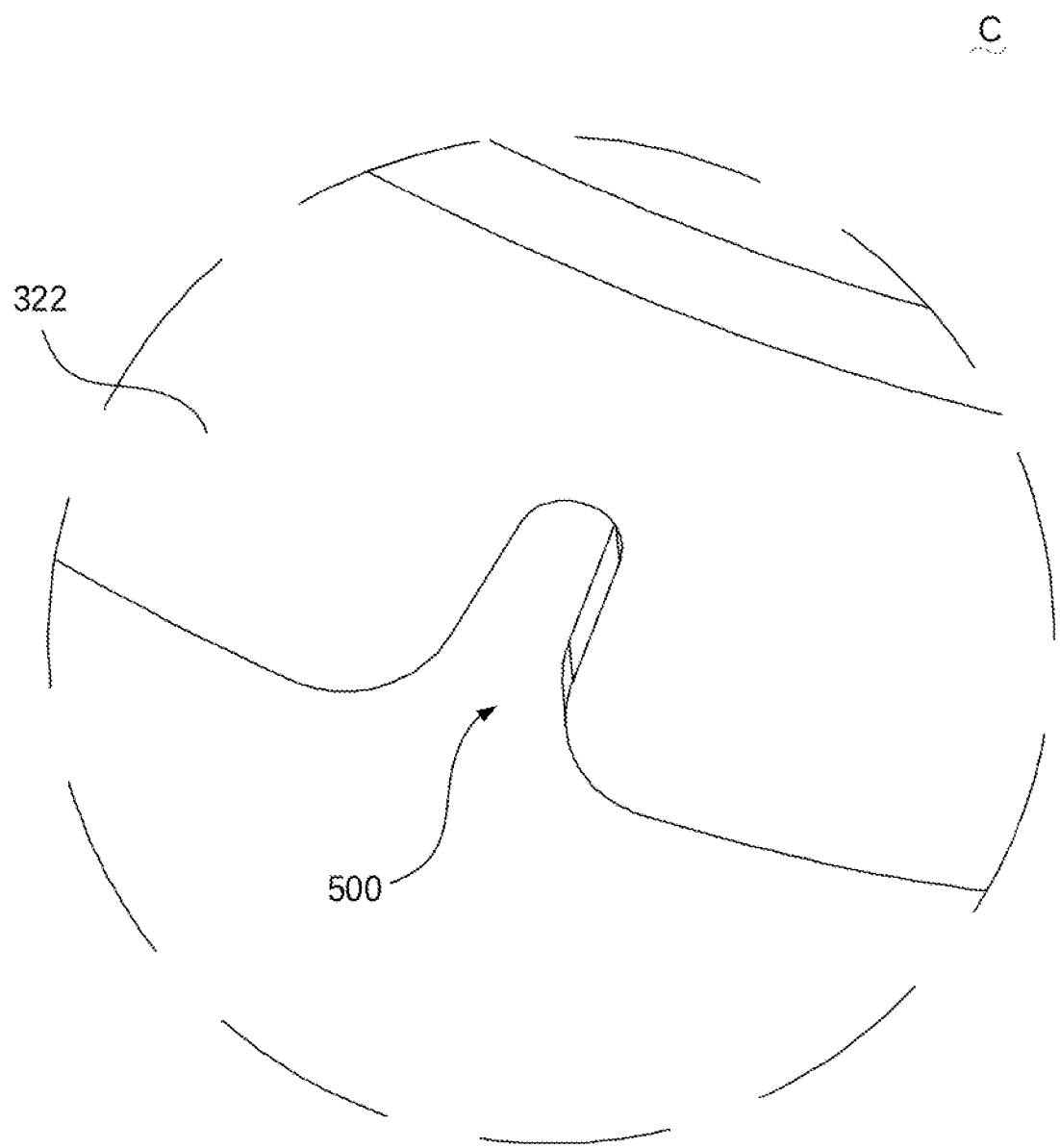
FIG. 9 is a schematic diagram of the enlarged structure of part C in FIG. 7.
Figure 10:
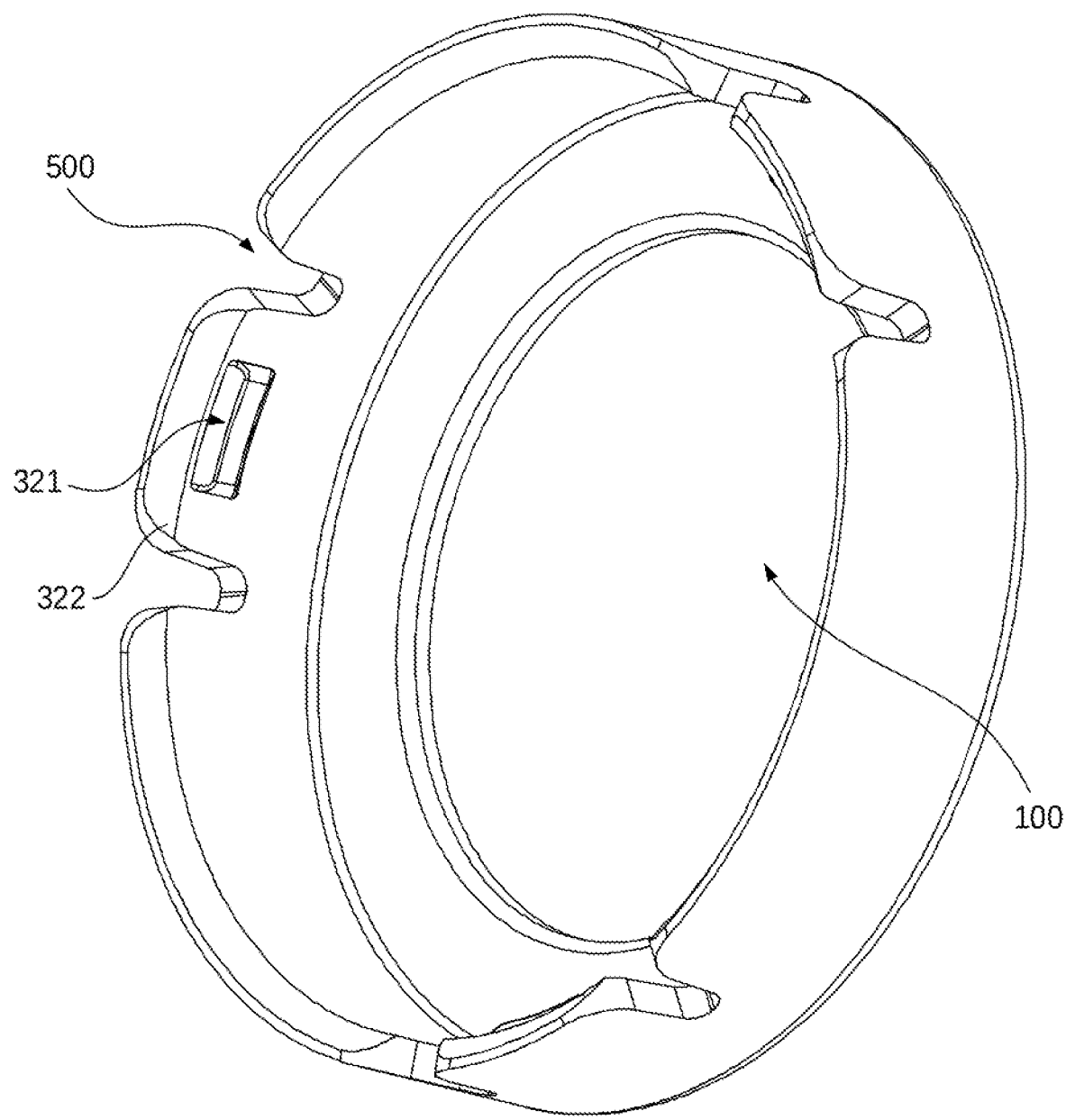
FIG. 10 is a schematic diagram of the fixing piece in the ultrasonic device shown in FIG. 6.

Further, please refer to FIG. 6 to FIG. 10 together, the side of the peripheral wall 32 away from the cover plate 31 is provided with a plurality of through grooves 500, and the through grooves 500 run through the peripheral wall 32 to form elastic arm 322, and the second clamping part 321 are disposed on the elastic arm 322. In this way, through the arrangement of the through grooves 500, the elastic arm 322 with certain elasticity can be formed on the peripheral wall 32, and the connection stability between the second clamping part 321 and the ultrasonic head 20 can be improved. As shown in FIG. 9, further, the end of the through grooves 500 close to the cover plate 31 is arc-shaped, so as to avoid fracture at the end of the through groove 500 close to the cover plate 31 when the peripheral wall 32 is deformed by force. There is a circular arc transition between the two sides of the through groove 500 away from the end of the cover plate 31 and the peripheral wall 32. When replacing the ultrasonic coupling gel 40, the above setting can avoid scratching fingers when separating the fixing piece 30 from the ultrasonic head 20 Furthermore, the above arrangement makes the through grooves 500 have a small end close to the end of the cover plate 31 and a large end far away from the end of the cover plate 31, so as to facilitate the elastic deformation of the elastic arm 322. Further, there is a round transition between the peripheral wall 32 and the cover plate 31 to reduce the risk of the ultrasonic device scratching the skin.

Further, please refer to FIG. 7 and FIG. 9 together, the first clamping part 400 is an annular structure, which can reduce the assembly accuracy between the fixing piece 30 and the ultrasonic head 20 and improve the assembly efficiency. In this embodiment, the first clamping part 400 is an annular groove, and the second clamping part 321 is a protruding structure. It can be understood that in other embodiments, the first clamping part 400 is an annular protrusion, and the second clamping part 321 is a groove structure.

On the basis of the above-mentioned embodiment, the protruding part 42 is attached to the inner wall of the through hole 100 on the cover plate, so that the circumferential direction of the protruding part 42 can be attached to the cover plate 31, and the rigidity of the protruding part 42 is improved to avoid or reduce the risk of breakage at the junction of the connecting part 41 and the protruding part 42.

In some embodiments, please refer to FIG. 2, FIG. 4, and FIG. 7, the ultrasonic head 20 includes a first surface 21, and the connecting part 41 is attached to the first surface 21 to ensure the conduction of ultrasound. In this embodiment, the first surface 21 is a plane surface. It can be understood that in other embodiments, the first plane may also be a curved surface.

In some embodiments, please refer to FIG. 2, FIG. 4, FIG. 7, and FIG. 8, the first surface 21 is provided with rounded corners 22 bent toward the body 10 in the circumferential direction. In FIG. 2 and FIG. 4, the rounded corners 22 can guide and cooperate with the peripheral wall 32 to realize the rapid assembly of the fixing piece 30 and the ultrasonic head 20. In FIG. 7 and FIG. 8, the rounded corners 22 can guide and cooperate with the second clamping part 321 in a protruding structure to realize quick assembly of the fixing piece 30 and the ultrasonic head 20.

Figure 11:
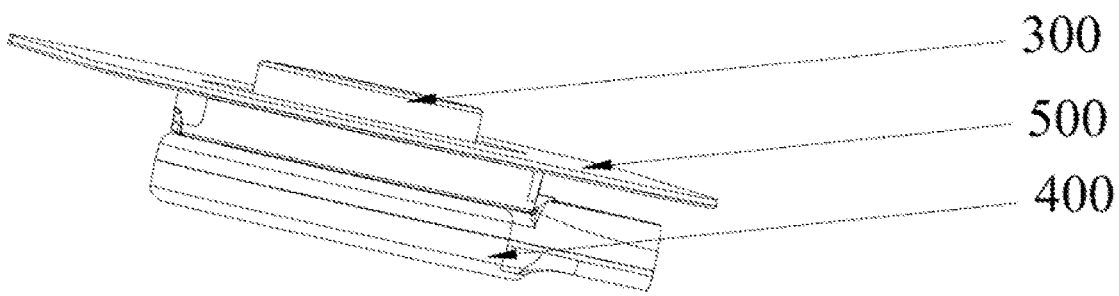
FIG. 11 is a partial schematic view of the ultrasonic device in the fourth embodiment.
Figure 12:
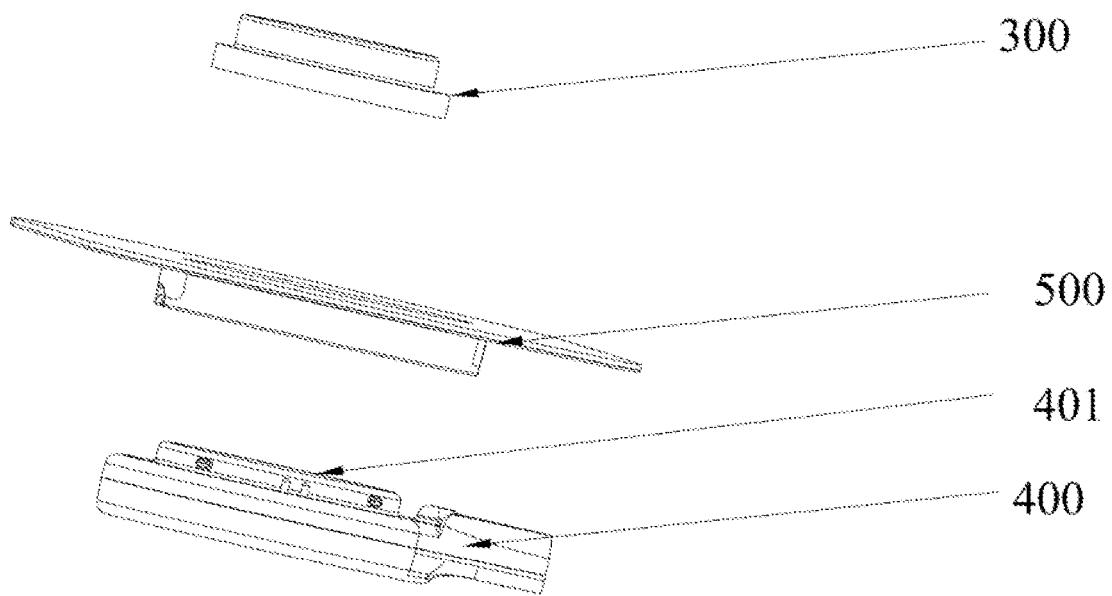
FIG. 12 is an exploded view an exploded view of FIG. 11.

In the fourth embodiment, please refer to FIG. 11 and FIG. 12 to describe the ultrasonic device provided by the present invention. The ultrasonic device includes an ultrasonic coupling gel 300, an ultrasonic head 400, an ultrasonic head output part 401, and an ultrasonic fixing sticker 500. Wherein, the ultrasonic head 400 can be connected to the body through an output line, and the ultrasonic fixing sticker 500 can be attached to different portions of the human body. In this embodiment, a cavity is provided inside the ultrasonic head 400 for installation of electrical components such as circuit boards and power supplies. In other embodiments, the ultrasonic head 400 can also be other carrier structures (such as a handheld or a wireless connection structure) for carrying the ultrasonic fixing sticker 500 and the ultrasonic coupling gel 300. Further, the ultrasonic head output part 401 protruded from the ultrasonic head 400. The ultrasound head output part 401 is capable of generating ultrasound. There is a through hole on the ultrasonic fixing sticker 500. One side of the ultrasonic coupling gel 300 is attached to the ultrasonic head 400, and the other side acts on the treatment site of the human body through the through hole of the ultrasonic fixing sticker 500 to ensure the conduction of ultrasound. In this embodiment, the ultrasonic coupling gel 300 is made of solid coupling gel. The ultrasonic coupling gel 300 has a certain degree of elasticity to improve the comfort of contact with the skin and avoid scratching it. At the same time, the ultrasonic coupling gel 300 can make the ultrasonic head 400 contact with the skin to reduce acoustic resistance, reduce the reflection loss of ultrasonic energy on the skin, and play a lubricating role. It can be understood that in other embodiments, the ultrasonic coupling gel 300 can be replaced by other solid gels, including but not limited to coupling gels, aqueous polymer gels, acrylic resin gels, or solid gels made of other materials.

These and other advantages of the invention will be further understood and appreciated by those skilled in the art by reference to the following written specification, claims and appended drawings.

Because many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalence.

What is claimed is:
1. An ultrasound device, comprising:
a body;
an ultrasonic head, which protrudes from the body and is configured to generate ultrasound;
a fixing piece, which comprises a cover plate and a peripheral wall circumferentially and vertically connected with the cover plate; the peripheral wall is sleeved on the ultrasonic head to form an accommodation space between the ultrasonic head and the cover plate; a through hole is provided on the cover plate, and the through hole communicates with the accommodation space; and
an ultrasonic coupling gel, which is used for ultrasound to pass through; the ultrasonic coupling gel comprises a connecting part and a protruding part; the connecting part is accommodated in the accommodation space and directly attached to the ultrasonic head and the cover plate respectively and simultaneously; the protruding part is arranged on the connecting part and is exposed outside the fixing piece through the through hole;
wherein the ultrasonic head comprises a first surface, the connecting part of the ultrasonic coupling gel is bonded to the first surface, and the first surface is a plane surface or a curved surface comprising rounded corners bending toward the body in a circumferential direction of the ultrasonic head;
wherein the ultrasonic head comprises a first clamping part, and the first clamping part is an annular groove that wraps around the entire ultrasonic head, wherein the peripheral wall of the fixing piece comprises a second clamping part, the second clamping part is a protruding structure, and the second clamping part protrudes into the annular groove to directly connect with the first clamping part;
wherein the round corners guide and cooperate with the second clamping part in the protruding structure to accelerate assemblance of the fixing piece and the ultrasonic head, and the peripheral wall is configured to be sleeved on the ultrasonic head;
wherein the peripheral wall comprises a first plurality of magnetic attractors evenly distributed along a circumferential direction of the peripheral wall, the ultrasonic head comprises a second plurality of magnetic attractors evenly distributed along the circumferential direction of the ultrasonic head, the first plurality of magnetic attractors and the second plurality of magnetic attractors cooperate to ensure a uniform force between the fixing piece and the ultrasonic head;
wherein the first plurality of magnetic attractors are arranged on a surface of the peripheral wall other than a horizontal end surface of the peripheral wall, and the second plurality of magnetic attractors are arranged on a surface of the ultrasonic head other than a horizontal end surface of the ultrasonic head; and
wherein the peripheral wall comprises one or more vacant portions, the one or more vacant portions are arranged on a side of the peripheral wall that is away from the cover plate, and the first plurality of the magnetic attractors are arranged to be disjoint from the one or more vacant portions.

2. The ultrasound device of claim 1, wherein, the peripheral wall elastically abuts against the ultrasonic head, and the arc-shaped vacant portion is arc shaped.

3. The ultrasound device of claim 1, wherein, the protruding part is attached to inner wall of the through hole on the cover plate.

4. The ultrasound device according to claim 1, wherein the one or more vacant portions comprise a plurality of vacant portions, and the plurality of vacant portions are unevenly distributed.

5. The ultrasound device according to claim 1, wherein a setting of the second clamping part and the first clamping part is configured to act as a stopper to limit the fixing piece from continuing to move toward a side of the ultrasonic head, and to prevent the ultrasonic coupling gel from being squeezed, deformed, or crushed.

6. The ultrasound device according to claim 1, wherein each of the one or more vacant portions comprises a small end close to the end of the cover plate and a large end far away from the end of the cover plate, so as to facilitate elastic deformation of the peripheral wall;
wherein the small end is arc-shaped, so as to avoid fracture and further facilitate the elastic deformation of the peripheral wall; and
wherein a circular arc-transition is disposed between two sides of the each of the one or more vacant portions away from an end of the cover plate and the peripheral wall, so as to further facilitate the replacement of the ultrasonic gel and to avoid scratching body parts.

7. The ultrasound device of claim 1, wherein, the ultrasonic coupling gel comprises water-based polymer gel or acrylic resin gel.

8. The ultrasound device of claim 7, wherein, the peripheral wall elastically abuts against the ultrasonic head, and the vacant portion is arc shaped.

9. The ultrasound device of claim 7, wherein, the protruding part is attached to inner wall of the through hole on the cover plate.

10. The ultrasound device of claim 1, wherein, the ultrasonic head is provided with an annular notch to form a stepped portion in combination with the rounded corners on the ultrasonic head, and a side of the peripheral wall that is away from the cover plate is complementary to the annular notch.

11. The ultrasound device of claim 10, wherein, the peripheral wall elastically abuts against the ultrasonic head, and the vacant portion is arc shaped.

12. An ultrasound apparatus assembling method, comprising:
arranging an ultrasonic head to protrude from a body, wherein the ultrasonic head is configured to generate ultrasound;
circumferentially and vertically connecting a peripheral wall with a cover plate to form a fixing piece;
sleeving the peripheral wall of the fixing piece on the ultrasonic head to form an accommodation space between the ultrasonic head and the cover plate;
providing a through hole on the cover plate so that the through hole communicates with the accommodation space;
attaching a connecting part and a protruding part to form an ultrasonic coupling gel, which is used for ultrasound to pass through;
accommodating the connecting part in the accommodation space so that the connecting part is directly attached to the ultrasonic head and the cover plate respectively and simultaneously; and
arranging the protruding part on the connecting part so that the protruding part is exposed outside the fixing piece through the through hole;
wherein the ultrasonic head comprises a first surface, the connecting part of the ultrasonic coupling gel is bonded to the first surface, and the first surface is a plane surface or a curved surface comprising rounded corners bending toward the body in a circumferential direction of the ultrasonic head;
wherein the ultrasonic head comprises a first clamping part, and the first clamping part is an annular groove that wraps around the entire ultrasonic head, wherein the peripheral wall of the fixing piece comprises a second clamping part, the second clamping part is a protruding structure, and the second clamping part protrudes into the annular groove to directly connect with the first clamping part, the round corners guide and cooperate with the second clamping part in the protruding structure to accelerate assemblance of the fixing piece and the ultrasonic head, and the peripheral wall is configured to be sleeved on the ultrasonic head;
wherein the peripheral wall comprises a first plurality of magnetic attractors evenly distributed along a circumferential direction of the peripheral wall, the ultrasonic head comprises a second plurality of magnetic attractors evenly distributed along the circumferential direction of the ultrasonic head, the first plurality of magnetic attractors and the second plurality of magnetic attractors cooperate to ensure a uniform force between the fixing piece and the ultrasonic head;
wherein the first plurality of magnetic attractors are arranged on a surface of the peripheral wall other than a horizontal end surface of the peripheral wall, and the second plurality of magnetic attractors are arranged on a surface of the ultrasonic head other than a horizontal end surface of the ultrasonic head;

wherein the peripheral wall comprises one or more vacant portions, the one or more vacant portions are arranged on a side of the peripheral wall that is away from the cover plate, and the first plurality of the magnetic attractors are arranged to be disjoint from the one or more vacant portions.

13. The ultrasound apparatus assembling method according to claim 12, wherein the one or more vacant portions comprise a plurality of vacant portions, and the method further comprises:

configuring the plurality of vacant portions to be unevenly distributed.

14. The ultrasound apparatus assembling method according to claim 12, further comprising:

configuring a setting of the second clamping part and the first clamping part to act as a stopper to limit the fixing piece from continuing to move toward a side of the ultrasonic head, and to prevent the ultrasonic coupling gel from being squeezed, deformed, or crushed.

15. The ultrasound apparatus assembling method according to claim 12, further comprising:

configuring each of the one or more vacant portions to comprise a small end close to the end of the cover plate and a large end far away from the end of the cover plate, so as to facilitate elastic deformation of the peripheral wall;

configuring the small end to be arc-shaped, so as to avoid fracture and further facilitate the elastic deformation of the peripheral wall; and disposing a circular arc-transition between two sides of the each of the one or more vacant portions away from an end of the cover plate and the peripheral wall, so as to further facilitate the replacement of the ultrasonic gel and to avoid scratching body parts.

16. The ultrasound apparatus assembling method according to claim 12, further comprising:

manufacturing the ultrasonic coupling gel with water-based polymer gel or acrylic resin gel.

17. The ultrasound apparatus assembling method according to claim 16, further comprising:

providing the ultrasonic head with an annular notch to form a stepped portion in combination with the rounded corners on the ultrasonic head, and arranging a side of the peripheral wall that is away from the cover plate to be complementary to the annular notch.

18. An ultrasound device assembling method, comprising:

assembling a body;

arranging an ultrasonic head to protrude from the body, wherein the ultrasonic head is configured to generate ultrasound;

arranging a fixing piece, wherein the fixing piece comprises a cover plate and a peripheral wall circumferentially connected with the cover plate, and arranging the fixing piece comprises sleeving the peripheral wall on the ultrasonic head to form an accommodation space between the ultrasonic head and the cover plate;

providing a through hole on the cover plate, and configuring the through hole to communicate with the accommodation space; and arranging an ultrasonic coupling gel configured for ultrasound to pass through, wherein the ultrasonic coupling gel comprises a connecting part and a protruding part, the connecting part is accommodated in the accommodation space and attached to the ultrasonic head and the cover plate respectively, and arranging the ultrasonic gel comprises arranging the protruding part on the connecting part and exposing the protruding part outside the fixing piece through the through hole; and arranging one or more vacant portions on a side of the peripheral wall that is away from the cover plate;

wherein the one or more vacant portions penetrate partially in a vertical direction through the peripheral wall to facilitate replacement of the ultrasonic gel; and wherein heights of the one or more vacant portions are less than a height of the peripheral wall, and the one or more vacant portions are disjoint from of the cover plate of the fixing piece;

wherein the peripheral wall comprises a first plurality of magnetic attractors evenly distributed along a circumferential direction of the peripheral wall, the ultrasonic head comprises a second plurality of magnetic attractors evenly distributed along a circumferential direction of the ultrasonic head, the first plurality of magnetic attractors and the second plurality of magnetic attractors cooperate to ensure a uniform force between the fixing piece and the ultrasonic head;

wherein the first plurality of magnetic attractors are arranged on a surface of the peripheral wall other than a horizontal end surface of the peripheral wall, and the second plurality of magnetic attractors are arranged on a surface of the ultrasonic head other than a horizontal end surface of the ultrasonic head; and wherein the first plurality of the magnetic attractors are arranged to be disjoint from the one or more vacant portions.

19. The ultrasound device assembling method according to claim 18, wherein the one or more vacant portions comprise a plurality of vacant portions, and the method further comprises:

configuring the plurality of vacant portions to be unevenly distributed.

20. The ultrasound device assembling method according to claim 18, further comprising:

configuring each of the one or more vacant portions to comprise a small end close to the end of the cover plate and a large end far away from the end of the cover plate, so as to facilitate elastic deformation of the peripheral wall;

configuring the small end to be arc-shaped, so as to avoid fracture and further facilitate the elastic deformation of the peripheral wall; and disposing a circular arc-transition between two sides of the each of the one or more vacant portions away from an end of the cover plate and the peripheral wall, so as to further facilitate the replacement of the ultrasonic gel and to avoid scratching body parts.

* * * * *